United States Patent
Ichimura et al.

(10) Patent No.: US 9,963,426 B1
(45) Date of Patent: May 8, 2018

(54) PROCESS FOR PRODUCING ALLYL-SUBSTITUTED BISPHENOL COMPOUND

(71) Applicant: NICCA CHEMICAL CO., LTD., Fukui-shi, Fukui (JP)

(72) Inventors: Kenta Ichimura, Fukui (JP); Mikihiko Kurose, Fukui (JP)

(73) Assignee: NICCA CHEMICAL CO., LTD., Fukui-shi, Fukui (JP)

( * ) Notice: Subject to any disclaimer, the term of this patent is extended or adjusted under 35 U.S.C. 154(b) by 0 days. days.

(21) Appl. No.: 15/569,298

(22) PCT Filed: Apr. 21, 2016

(86) PCT No.: PCT/JP2016/062654
§ 371 (c)(1),
(2) Date: Oct. 25, 2017

(87) PCT Pub. No.: WO2016/175128
PCT Pub. Date: Nov. 3, 2016

(30) Foreign Application Priority Data

Apr. 27, 2015 (JP) ................. 2015-090605

(51) Int. Cl.
C07C 315/04 (2006.01)

(52) U.S. Cl.
CPC .................. *C07C 315/04* (2013.01)

(58) Field of Classification Search
CPC .................................................. C07C 315/04
See application file for complete search history.

(56) References Cited

U.S. PATENT DOCUMENTS

| | | | |
|---|---|---|---|
| 3,014,968 A | 12/1961 | Kaiser et al. | |
| 2006/0217574 A1 | 9/2006 | Enokida et al. | |

FOREIGN PATENT DOCUMENTS

| | | |
|---|---|---|
| JP | S60-169456 A | 9/1885 |
| JP | H05-65239 S | 3/1993 |
| JP | H05-65240 A | 3/1993 |
| JP | 2005/075757 A | 3/2005 |
| JP | 2008/110945 A | 5/2008 |

OTHER PUBLICATIONS

The International Bureau of WIPO, International Preliminary Report on Patentability in International Application No. PCT/JP2016/062654 dated Nov. 9, 2017.
Japanese Patent Office, International Search Report in PCT Application No. PCT/JP2016/062654, dated Jul. 12, 2016.
Nelson, S.G., et al., "Catalyzed Olefin Isomerization Leading to Highly Stereoselective Claisen Rearrangements of Aliphatic Allyl Vinyl Ethers", *American Chemical Society*, 125(43), p. 13000-p. 13001 (2003).
Takai, K., et al., "Aliphatic Claisen Rearrangement Promoted by Organoaluminium Compounds", *Tetrahedron Letters*, 22(40), p. 3985-3988 (1981).

*Primary Examiner* — Rosalynd A Keys
(74) *Attorney, Agent, or Firm* — Leydig Voit & Mayer

(57) ABSTRACT

The present invention relates to a process for producing an allyl-substituted bisphenol compound including a step of subjecting a diallyl etherified bisphenol compound represented by the following general formula (I) to a thermal rearrangement reaction in the presence of a specific phosphine compound (I)

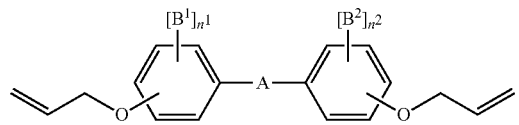

[in the formula, A represents a single bond, $-SO_2-$, $-S-$, $-O-$, a divalent group represented by the following formula (i-1), or a divalent group represented by $-CY^1Y^2-$ ($Y^1$ and $Y^2$ each independently represent hydrogen, a linear, branched, or cyclic alkyl group having 6 or less carbon atoms, a phenyl group, or an aralkyl group having 7 or 8 carbon atoms), $B^1$ and $B^2$ each independently represent a linear, branched, or cyclic alkyl group having 6 or less carbon atoms, an allyl group, a phenyl group, or an aralkyl group having 7 or 8 carbon atoms, and $n^1$ and $n^2$ each independently represent an integer from 0 to 2, (i-1)

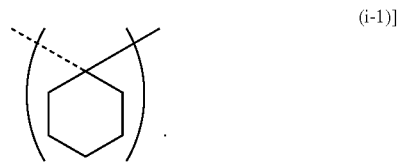

2 Claims, No Drawings

PROCESS FOR PRODUCING ALLYL-SUBSTITUTED BISPHENOL COMPOUND

CROSS-REFERENCE TO RELATED APPLICATIONS

This patent application is the U.S. National Stage of International Application No. PCT/JP2016/062654, filed Apr. 21, 2016, which claims the benefit of Japanese Application No. 2015-090605, filed Apr. 27, 2015, which are each incorporated by reference.

TECHNICAL FIELD

The present invention relates to a process for producing an allyl-substituted bisphenol compound.

BACKGROUND ART

Hitherto, allyl-substituted bisphenol compounds are useful substances as a developer of a thermosensitive recording material, a polymer additive, and the like, and various production processes thereof have been attempted. As the production process, for example, a process for producing an allyl-substituted bisphenol compound by subjecting a diallyl etherified bisphenol compound to a thermal rearrangement reaction is known.

For example, in Patent Literature 1, a process is described in which 4,4'-dihydroxydiphenyl sulfone or an alkali metal salt thereof is reacted with an allyl halide to be converted into 4,4'-diallyloxydiphenyl sulfone of a diallyl etherified bisphenol compound and the 4,4'-diallyloxydiphenyl sulfone thus obtained is then subjected to a thermal rearrangement reaction, thereby producing 3,3-diallyl-4,4'-dihydroxydiphenyl sulfone of an allyl-substituted bisphenol compound.

In addition, a process intended to suppress by-production of impurities and to obtain an allyl-substituted bisphenol compound at a high yield has also been investigated. For example, in Patent Literature 2, a process for performing the Claisen rearrangement reaction in the presence of a basic compound such as an aniline derivative is disclosed. In Patent Literature 3, a process for performing a thermal rearrangement reaction in the presence of a chelating agent, and the like are disclosed.

CITATION LIST

Patent Literature

Patent Literature 1: Japanese Unexamined Patent Publication No. S60-169456
Patent Literature 2: Japanese Unexamined Patent Publication No. H5-65240
Patent Literature 3: Japanese Unexamined Patent Publication No. 2005-075757

SUMMARY OF INVENTION

Technical Problem

However, in the above production processes, a tendency that the reaction product obtained by the reaction is colored black or brown is strongly observed and it is not satisfactory in terms of suppressing by-production of coloring impurities although it is possible to obtain the target product at a constant yield. Hence, in the case of performing decoloration or removal of impurities from the reaction product, it is required to perform a decoloration treatment by an adsorbent and the like, a purification treatment by recrystallization using an organic solvent, and the like, and there is thus a problem that it is economically disadvantageous because of an increase in number of steps, lengthening of the production time, and the like.

The present invention has been made in view of the above circumstances, and an object thereof is to provide a process capable of producing a high-quality allyl-substituted bisphenol compound at a high yield and suppressing coloration and by-production of impurities.

Solution to Problem

As a result of extensive studies to solve the above problems, the present inventors have found out that coloration and by-production of impurities are suppressed and an allyl-substituted bisphenol compound is obtained at a high yield by subjecting a diallyl etherified bisphenol compound to a thermal rearrangement reaction in the presence of a specific phosphine compound, thereby completing the present invention.

In other words, the present invention provides a process for producing an allyl-substituted bisphenol compound including a step of subjecting a diallyl etherified bisphenol compound represented by the following general formula (I) to a thermal rearrangement reaction in the presence of a phosphine compound represented by the following general formula (II):

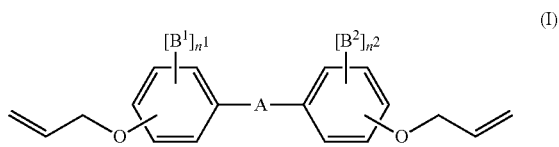

[in the formula, A represents a single bond, —$SO_2$—, —S—, —O—, a divalent group represented by the following formula (i-1), or a divalent group represented by —$CY^1Y^2$— ($Y^1$ and $Y^2$ each independently represent hydrogen, a linear, branched, or cyclic alkyl group having 6 or less carbon atoms, a phenyl group, or an aralkyl group having 7 or 8 carbon atoms), $B^1$ and $B^2$ each independently represent a linear, branched, or cyclic alkyl group having 6 or less carbon atoms, an allyl group, a phenyl group, or an aralkyl group having 7 or 8 carbon atoms, and $n^1$ and $n^2$ each independently represent an integer from 0 to 2,

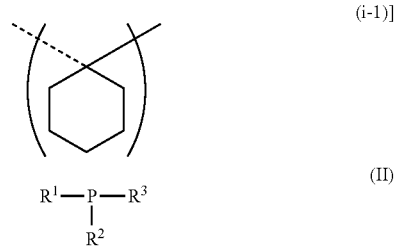

[in the formula, $R^1$, $R^2$, and $R^3$ each independently represent a linear, branched, or cyclic alkyl group having from 6 to 10 carbon atoms, an aryl group having from 6 to 14 carbon atoms, or an aralkyl group having 7 or 8 carbon atoms].

It is preferable that an antioxidant is further present in the step described above. It is possible to further suppress coloration of the reaction product accompanying advance of the reaction by subjecting the diallyl etherified bisphenol compound to the thermal rearrangement reaction in the presence of the specific phosphine compound and an antioxidant.

Advantageous Effects of Invention

According to the present invention, it is possible to provide a production process capable of suppressing coloration and by-production of impurities at the time of the thermal rearrangement reaction of a diallyl etherified bisphenol compound and thus obtaining a high-quality allyl-substituted bisphenol compound at a high yield. In other words, the allyl-substituted bisphenol compound obtained by the production process of the present invention is less colored, and it is thus possible to decrease the amount of adsorbent to be used in the subsequent decoloration step or to omit the decoloration step itself. In addition, the allyl-substituted bisphenol compound obtained by the production process of the present invention has a low content of impurities, and it is thus possible to more conveniently perform the purification step of the reaction product and to decrease the production loss of the target product or to shorten the production time.

DESCRIPTION OF EMBODIMENTS

Hereinafter, an embodiment for carrying out the present invention (hereinafter referred to as the "present embodiment") will be described in detail. It should be noted that the present invention is not limited to the following embodiments.

The process for producing an allyl-substituted bisphenol compound of the present embodiment includes a step of subjecting a diallyl etherified bisphenol compound represented by the following general formula (I) to a thermal rearrangement reaction in the presence of a phosphine compound represented by the following general formula (II).

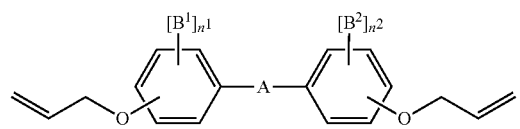

(I)

In the formula, A represents a single bond, —$SO_2$—, —S—, —O—, a divalent group represented by the following formula (i-1), or a divalent group represented by —$CY^1Y^2$— ($Y^1$ and $Y^2$ each independently represent hydrogen, a linear, branched, or cyclic alkyl group having 6 or less carbon atoms, a phenyl group, or an aralkyl group having 7 or 8 carbon atoms), $B^1$ and $B^2$ each independently represent a linear, branched, or cyclic alkyl group having 6 or less carbon atoms, an allyl group, a phenyl group, or an aralkyl group having 7 or 8 carbon atoms, and $n^1$ and $n^2$ each independently represent an integer from 0 to 2.

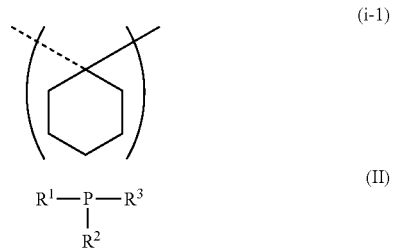

In the formula, $R^1$, $R^2$, and $R^3$ each independently represent a linear, branched, or cyclic alkyl group having from 6 to 10 carbon atoms, an aryl group having from 6 to 14 carbon atoms, or an aralkyl group having 7 or 8 carbon atoms.

In the general formula (I), A is preferably —$SO_2$— or —$CY^1Y^2$— and more preferably —$SO_2$— from the viewpoint of further improving the yield of the reaction product and further suppressing coloration and by-production of impurities. In a case in which A is —$CY^1Y^2$—, $Y^1$ and $Y^2$ are each independently preferably hydrogen or a linear, branched, or cyclic alkyl group having 6 or less carbon atoms, more preferably a linear, branched, or cyclic alkyl group having 6 or less carbon atoms, and still more preferably a linear alkyl group having 2 or less carbon atoms from the viewpoint of further improving the yield of the reaction product and further suppressing coloration and by-production of impurities.

$B^1$ and $B^2$ are each independently preferably an alkyl group having 6 or less carbon atoms or an allyl group from the viewpoint of further improving the yield of the reaction product and further suppressing coloration and by-production of impurities. From the viewpoint of further improving the yield of the reaction product, $n^1$ and $n^2$ are each independently preferably from 0 to 1 and more preferably 0. The bonding positions of $B^1$ and $B^2$ are each independently preferably positions which are not an ortho position or a para position with respect to the allyloxy group and more preferably a position which is not an ortho position with respect to the allyloxy group from the viewpoint of further improving the yield of the reaction product.

The diallyl etherified bisphenol compound represented by the general formula (I) according to the present embodiment can be appropriately selected according to the allyl-substituted bisphenol compound to be obtained. For example, in the case of producing 3,3'-diallyl-4,4'-dihydroxydiphenyl sulfone, 4,4'-diallyloxydiphenyl sulfone can be selected as the diallyl etherified bisphenol compound.

Specific examples of the diallyl etherified bisphenol compound represented by the general formula (I) may include 4,4'-diallyloxydiphenyl sulfone, 4,4'-diallyloxydiphenylmethane, 2,2'-(4,4'-diallyloxydiphenyl)propane, 3,3'-(4,4'-diallyloxydiphenyl)pentane, 4,4'-diallyloxybiphenyl, 4,4'-diallyloxydiphenyl ether, 4,4'-diallyloxydiphenyl thioether, 1,1'-4,4'-diallyloxydiphenyl)cyclohexane, 2,4'-diallyloxydiphenyl sulfone, 2,4'-diallyloxydiphenylmethane, 2,2'-(2,4'-diallyloxydiphenyl)propane, 2,4'-diallyloxybiphenyl, 2,4'-diallyloxydiphenyl ether, 2,4'-diallyloxydiphenyl thioether, 1,1'-(2,4'-diallyloxydiphenyl)cyclohexane, 3,3'-diallyl-4,4'-diallyloxydiphenyl sulfone, 2,2'-(3,3'-diallyl-4,4'-diallyloxydiphenyl)propane, and 3,3'-methyl-4,4'-diallyloxydiphenyl sulfone. Among them, for example, 4,4'-diallyloxydiphenyl sulfone, 4,4'-diallyloxydiphenylmethane, 2,2'-(4,4'-diallyloxydiphenyl)propane, 1,1'-(4,4'-diallyloxydiphenyl)cyclohexane, and 2,4'-diallyloxydiphenyl sulfone are preferable and 4,4'-diallyloxydiphenyl sulfone and 2,2'-(4,4'-diallyloxydiphenyl)propane are more preferable as the diallyl etherified bisphenol compound represented by the general formula (I) from the viewpoint that the diallyl etherified bisphenol compound itself is hardly decomposed by heat in the case of conducting the thermal rearrangement reaction under a solventless condition.

These diallyl etherified bisphenol compounds represented by the general formula (I) can be synthesized by those skilled in the art by using available raw materials and combining ordinary reactions. For example, the diallyl etherified bisphenol compound represented by the general formula (I) can be easily produced by a process in which the corresponding bisphenol compound is reacted with the corresponding allyl halide under an alkaline condition.

It is possible to advance the reaction while suppressing coloration of the reaction product and by-production of impurities as the phosphine compound represented by the general formula (II) according to the present embodiment is present in the system of the thermal rearrangement reaction of the diallyl etherified bisphenol compound represented by the general formula (I).

In the general formula (II), $R^1$, $R^2$, and $R^3$ are each independently preferably a linear, branched, or cyclic alkyl group having from 6 to 8 carbon atoms or an aryl group having from 6 to 14 carbon atoms, more preferably an aryl group having from 6 to 14 carbon atoms, and still more preferably an aryl group having from 6 to 8 carbon atoms from the viewpoint of farther improving the yield of the reaction product and further suppressing coloration and by-production of impurities.

Specific examples of the phosphine compound represented by the general formula (II) may include triphenylphosphine, tri-n-octylphosphine, tri-p-tolylphosphine, tri-3,5-xylylphosphine, diphenylcyclohexylphosphine, and tribenzylphosphine. These phosphine compounds represented by the general formula (II) can be used singly or in combination of two or more kinds thereof.

The amount of the phosphine compound represented by the general formula (II) blended is not particularly limited. The amount of the phosphine compound represented by the general formula (II) blended is preferably from 0.01 to 10 parts by mass, more preferably from 0.05 to 5 parts by mass, and still more preferably from 0.08 to 2 parts by mass with respect to 100 parts by mass of the diallyl etherified bisphenol compound from the viewpoint of further improving the yield of the reaction product and further suppressing coloration and by-production of impurities.

As the present embodiment, an antioxidant may be further present in the step of subjecting the diallyl etherified bisphenol compound represented by the general formula (I) to a thermal rearrangement reaction in the presence of the phosphine compound represented by the general formula (II). In the case of using an antioxidant, there is a tendency that coloration accompanying advance of the reaction can be further suppressed.

The antioxidant according to the present embodiment is not particularly limited, and generally used antioxidants can be used. Examples of the antioxidant may include a phenolic antioxidant such as hydroquinone monomethyl ether, hydroquinone monoethyl ether, 3,5-di-t-butyl-4-hydroxytoluene, 2,2'-methylenebis(6-t-butyl-3-methylphenol), or 1,1,3-tris(2-methyl-4-hydroxy-5-t-butylphenyl) butane, a sulfur-based antioxidant such as didodecyl 3,3'-thiodipropionate, ditetradecyl 3,3'-thiodipropionate, or dioctadecyl 3,3'-thiodipropionate, and a phosphorus-based antioxidant other than the phosphine compound represented by the general formula (II) such as triphenyl phosphite, diphenyl isodecyl phosphite, or tris(nonylphenyl) phosphite. Among them, a phenolic antioxidant is preferable, hydroquinone monomethyl ether and 3,5-di-t-butyl-4-hydroxytoluene are more preferable, and 3,5-di-t-butyl-4-hydroxytoluene is still more preferable as the antioxidant from the viewpoint of further improving the yield of the reaction product and further suppressing coloration and by-production of impurities. These antioxidants can be used singly or in combination of two or more kinds thereof.

The amount of the antioxidant blended is preferably from 0.01 to 10 parts by mass, more preferably from 0.05 to 5 parts by mass, and still more preferably from 0.08 to 2 parts by mass with respect to 100 parts by mass of the diallyl etherified bisphenol compound from the viewpoint of further improving the yield of the reaction product and further suppressing coloration and by-production of impurities.

In the production process of the present embodiment, by-production of impurities tends to be promoted by the thermal rearrangement reaction when an alkaline substance is present in the reaction step. Examples of the cause of the presence of an alkaline substance may include remaining, mixing, and the like of the alkaline substance in the course of production. For example, the diallyl etherified bisphenol compound represented by the general formula (I) according to the present embodiment is produced under an alkaline condition in some cases, and it is thus considered that there is a case in which the alkaline substances in the raw materials remain in a small amount even if purification and washing are performed. In an embodiment of the present invention, the thermal rearrangement reaction may be conducted by adding an acid in the reaction step for the purpose of avoiding the above-mentioned influence due to the presence of an alkaline substance in the reaction step. By adding an acid in the reaction step, there is a tendency that the alkaline substances in the system are neutralized, by-production of impurities is further suppressed, and the allyl-substituted bisphenol compound is obtained at a higher yield. Examples of the alkaline substance may include a hydroxide or a carbonate of an alkali metal or an alkaline earth metal and an alkali metal or alkaline earth metal salt of a bisphenol compound of a raw material in the production of a diallyl etherified bisphenol compound or a monoallyl etherified bisphenol compound of an intermediate.

The acid according to the present embodiment is not particularly limited, and generally used acids can be used. Examples of the acid may include an inorganic acid such as hydrochloric acid, sulfuric acid, phosphoric acid, phosphorous acid, or nitric acid and an organic acid such as formic acid, acetic acid, butyric acid, oxalic acid, citric acid, malic acid, tartaric acid, benzoic acid, benzenesulfonic acid, or p-toluenesulfonic acid. As the acid, sulfuric acid or phosphoric acid is preferable from the viewpoint of further improving the yield of the reaction product and further suppressing by-production of impurities. These acids can be used singly or M combination of two or more kinds thereof.

The amount of acid blended is not particularly limited, and those skilled in the art can appropriately design. For example, in a case in which it is previously known that an alkaline substance is present in the diallyl etherified bisphenol compound to be a raw material, the amount of acid blended is preferably from 0.5 to 20 molar equivalents, more preferably from 0.9 to 10 molar equivalents, and still more preferably from 1 to 3 molar equivalents with respect to the alkaline substance contained in the diallyl etherified bisphenol compound from the viewpoint of further improving the yield of the reaction product and further suppressing by-production of impurities.

The thermal rearrangement reaction of the diallyl etherified bisphenol compound according to the present embodiment may be conducted under a solventless condition or in an organic solvent. The thermal rearrangement reaction is preferably conducted under a solventless condition from the viewpoint of further improving the yield of the reaction product and further suppressing coloration and by-production of impurities. The thermal rearrangement reaction under a solventless condition means that the diallyl etherified bisphenol compound is melted by heating without adding an organic solvent and the like, the phosphine compound and the like are dissolved using this as a solvent, and the thermal rearrangement reaction is conducted in the reaction step.

In the case of using an organic solvent, the organic solvent to be used is not particularly limited as long as it is liquid at the reaction temperature, can dissolve the diallyl etherified bisphenol compound of a raw material, and does not inhibit the reaction. From the relationship with the reaction temperature, the organic solvent preferably has a boiling point of 160° C. or higher, more preferably has a boiling point of 180° C. or higher, and still more preferably has a boiling point of 200° C. or higher. As the organic solvent, an inert water-insoluble organic solvent such as a saturated aliphatic hydrocarbon solvent, an unsaturated hydrocarbon solvent, or an aromatic hydrocarbon solvent is preferable. The organic solvents can be used singly or in combination of two or more kinds thereof.

The saturated aliphatic hydrocarbon solvent may be any of a linear, branched, or cyclic saturated aliphatic hydrocarbon. Specific examples of the saturated aliphatic hydrocarbon solvent may include tridecane, hexadecane, octadecane, eicosane, docosane, triacontane, squalane, isodecane, isododecane, isotridecane, isohexadecane, cyclopentane, and cyclohexane. As the saturated aliphatic hydrocarbon solvent, it is also possible to use a mixture generally called paraffinic hydrocarbon, isoparaffinic hydrocarbon, or naphthenic hydrocarbon. Examples of a commercially available saturated aliphatic hydrocarbon may include IP SOLVENT series (trade name, manufactured by Idemitsu Kosan Co., Ltd.) and Diana Fresia series (trade name, manufactured by Idemitsu Kosan Co., Ltd.).

The unsaturated hydrocarbon solvent may be any of a linear, branched, or cyclic unsaturated hydrocarbon. Specific examples of the unsaturated aliphatic hydrocarbon solvent may include eicosene, henicosene, docosene, tricosene, and squalene.

Specific examples of the aromatic hydrocarbon solvent may include n-dodecylbenzene, n-tridecylbenzene, n-tetradecylbenzene, n-pentadecylbenzene, n-hexadecylbenzene, and diisopropylnaphthalene.

As the organic solvent as described above, a single component, a mixture of a plurality of components, or a mixture of those having certain specifications such as mineral oil, lubricating oil, kerosene, and light oil which are commercially available may be used. Among them, a paraffinic hydrocarbon or an isoparaffinic hydrocarbon is preferable as the organic solvent from the viewpoint of further improving the yield of the reaction product and further suppressing coloration and by-production of impurities.

The allyl-substituted bisphenol compound according to the present embodiment can be produced by mixing the diallyl etherified bisphenol compound represented by the formula (I) with the phosphine compound represented by the formula (II) and heating the mixture at a predetermined temperature. In the production process according to the present embodiment, in the case of using an antioxidant, an acid, an organic solvent, and the like, these may be mixed together with the diallyl etherified bisphenol compound represented by the formula (I) and the phosphine compound represented by the formula (II) in advance and the mixture may be then heated.

The heating method is not particularly limited as long as it can control the temperature. Examples of the heating method may include a heating method by heat conduction using a heat medium, an electric heater, and the like and a heating method by microwave irradiation using a microwave reaction apparatus and the like. These heating methods may be used concurrently.

The reaction temperature for the thermal rearrangement reaction may be equal to or higher than the temperature at which the diallyl etherified bisphenol compound represented by the formula (I) is melted or dissolved. The reaction temperature is preferably from 160 to 220° C., more preferably from 180 to 210° C., and still more preferably from 200 to 210° C. from the viewpoint of further improving the yield of the reaction product and further suppressing coloration and by-production of impurities.

The reaction time is changed depending on the scale of the reaction, the reaction temperature, the reactivity of the materials used, and the like, and it can be appropriately set by those skilled in the art. The reaction time is, for example, preferably from 5 to 36 hours, more preferably from 5.5 to 18 hours, and still more preferably from 6 to 9 hours from the viewpoint of further improving the yield of the reaction product and further suppressing coloration and by-production of impurities.

The pressure condition at the time of the reaction may be a normal pressure, reduced pressure, or pressurized condition. The pressure condition is not particularly limited, but it is preferably a normal pressure or pressurized condition from the viewpoint of further improving the yield of the reaction product and further suppressing coloration and by-production of impurities.

The atmosphere at the time of the reaction may be an air atmosphere, or it may be purged with an inert gas such as nitrogen or argon. The atmosphere is preferably purged with an inert gas from the viewpoint of further improving the yield of the reaction product and further suppressing coloration and by-production of impurities.

According to the production process of the present embodiment, it is possible to produce the allyl-substituted bisphenol compound of a target product at a high yield of preferably 75% or more, more preferably 80% or more, and still more preferably 90% or more while suppressing coloration accompanying advance of the reaction.

It is possible to confirm whether the reaction product after the thermal rearrangement reaction is the target allyl-substituted bisphenol compound or not by a method such as nuclear magnetic resonance (NMR) or high performance liquid chromatography (HPLC).

It is possible to obtain a higher-purity allyl-substituted bisphenol compound from the reaction product obtained as described above by purifying the reaction product through operations such as alkali extraction, solvent extraction, washing, acid precipitation, and recrystallization.

EXAMPLES

Hereinafter, the present invention will be described more specifically with reference to Examples. However, the present invention is not limited to these Examples.

<Calculation of Yield of Reaction Product>

In Examples and Comparative Examples, 3,3'-diallyl-4,4'-dihydroxydiphenyl sulfone of the target product was subjected to HPLC, the retention time of the peak at which this was detected was measured in advance, and the presence or absence of the target product was confirmed by the peak detected at the same time as this retention time when the reaction product was subjected to HPLC. The yield of the reaction product was expressed as the percentage of the peak area of the target product with respect to the total peak area on the HPLC chart. The measurement of HPLC was conducted under the following conditions.

(Measurement Conditions of HPLC)

Column: Shim-pack HRC-ODS (4.6 mm of inner diameter×250 mm of length, manufactured by SHIMADZU GLC Ltd.)

Mobile phase: 50% acetonitrile-water

Column temperature: 40° C.

Flow rate: 1.0 mL/min

Detector: SPD-10Avp (manufactured by SHIMADZU CORPORATION)

Detection wavelength: UV (254 nm)

Sample concentration: reaction product/mobile phase=25 mg/25 mL

<Confirmation of Coloration of Reaction Product>

In Examples and Comparative Examples, with regard to the coloration at the time of the thermal rearrangement reaction, the color of the reaction product in the molten or dissolved state immediately after the reaction was visually judged immediately under the indoor three-wavelength type daylight white fluorescent lamp. The criteria for judgement of coloration are presented below.

(Criteria for Judgement)

Favorable A: white to yellowish white

B: yellow

C: brown

Poor D: black

<Measurement of Concentration of Alkaline Substance Contained in Raw Material>

The concentration (ppm, weight ratio) of the alkaline substances remaining in 4,4'-diallyloxydiphenyl sulfone used as a raw material was measured by dissolving 30 g of 4,4'-diallyloxydiphenyl sulfone in 450 g of dimethylsulfoxide, adding 10 mL of 20 mmol/L hydrochloric acid thereto, then performing the neutralization titration by using a 20 mmol/L, aqueous solution of sodium hydroxide, comparing the result to that for the blank test, and converting the concentration of the remaining alkaline substances into the weight of sodium hydroxide. As a result of the measurement, the concentration of the alkaline substances remaining in 4,4'-diallyloxydiphenyl sulfone was 50 ppm.

Example 1

Into a four-necked flask, 250 g of 4,4'-diallyloxydiphenyl sulfone and 0.5 g of triphenylphosphine were charged and subjected to the thermal rearrangement reaction at from 205 to 210° C. for 7 hours in a nitrogen stream. After the reaction was completed, the temperature was lowered to 185° C., and the reaction product was taken into a metallic vessel and cooled to room temperature as it was. The reaction product thus obtained was diluted to a prescribed concentration and analyzed by HPLC, and as a result, the yield of 3,3'-diallyl-4,4'-dihydroxydiphenyl sulfone of the target product was 87.2%. The color of the reaction product in a molten state was yellow.

Example 2

The reaction was conducted under the same conditions as in Example 1 except that raw materials having the composition presented in Table 1 were charged, and the reaction product was analyzed by HPLC. As a result, the yield of 3,3'-diallyl-4,4'-dihydroxydiphenyl sulfone of the target product was 89.2%. The color of the reaction product in a molten state was white to yellowish white.

Example 3

The reaction was conducted under the same conditions as in Example 1 except that raw materials having the composition presented in Table 1 were charged, and the reaction product was analyzed by HPLC. As a result, the yield of 3,3'-diallyl-4,4'-dihydroxydiphenyl sulfone of the target product was 90.9%. The color of the reaction product in a molten state was white to yellowish white.

Example 4

The reaction was conducted under the same conditions as in Example 1 except that raw materials having the composition presented in Table 1 were charged, and the reaction product was analyzed by HPLC. As a result, the yield of 3,3'-diallyl-4,4'-dihydroxydiphenyl sulfone of the target product was 92.2%. The color of the reaction product in a molten state was white to yellowish white.

Example 5

The reaction was conducted under the same conditions as in Example 1 except that raw materials having the composition presented in Table 1 were charged, and the reaction product was analyzed by HPLC. As a result, the yield of 3,3'-diallyl-4,4'-dihydroxydiphenyl sulfone of the target product was 82.3%. The color of the reaction product in a molten state was yellow.

Example 6

The reaction was conducted under the same conditions as in Example 1 except that raw materials having the composition presented in Table 1 were charged, and the reaction product was analyzed by HPLC. As a result, the yield of 3,3'-diallyl-4,4'-dihydroxydiphenyl sulfone of the target product was 77.0%. The color of the reaction product in a molten state was white to yellowish white.

Comparative Example 1

The reaction was conducted under the same conditions as in Example 1 except that raw materials having the composition presented in Table 1 were charged, and the reaction product was analyzed by HPLC. As a result, the yield of 3,3'-diallyl-4,4'-dihydroxydiphenyl sulfone of the target product was 0.2%. The color of the reaction product in a molten state was brown.

Comparative Example 2

The reaction was conducted under the same conditions as in Example 1 except that raw materials having the composition presented in Table 1 were charged, and the reaction product was analyzed by HPLC. As a result, the yield of 3,3'-diallyl-4,4'-dihydroxydiphenyl sulfone of the target product was 3.9%. The color of the reaction product in a molten state was black.

TABLE 1

| | | | Example 1 | Example 2 | Example 3 | Example 4 | Example 5 | Example 6 | Comparative Example 1 |
|---|---|---|---|---|---|---|---|---|---|
| Composition of raw materials (g) | 4,4'-Diallyloxydiphenyl sulfone | | 250 | 250 | 250 | 250 | 90 | 250 | 250 |
| | Triphenylphosphine | | 0.5 | 0.5 | 0.5 | 0.5 | 0.9 | — | — |
| | Tri-n-octylphosphine | | — | — | — | — | — | 0.5 | — |
| | N,N-dimethylaniline | | — | — | — | — | — | — | — |
| | Trilauryl phosphite | | — | — | — | — | — | — | — |
| | Hydroquinone monomethyl ether | | — | 0.25 | 0.25 | — | — | — | — |
| | 3,5-Di-t-butyl-4-hydroxytoluene | | — | — | — | 0.25 | 0.18 | 0.5 | — |
| | 85% Phosphoric acid | | — | — | 0.07 | 0.07 | 0.02 | 0.07 | — |
| | Isoparaffinic hydrocarbon solvent | | — | — | — | — | 60 | — | — |
| | Paraffinic hydrocarbon solvent | | — | — | — | — | 60 | — | — |
| Reaction product | 3,3'-Diallyl-4,4'-dihydroxydiphenyl sulfone | Yield (%) | 87.2 | 89.2 | 90.9 | 92.2 | 82.3 | 77 | 0.2 |
| | | Coloration | B | A | A | A | B | A | C |

| | | | Comparative Example 2 | Comparative Example 3 | Comparative Example 4 | Comparative Example 5 |
|---|---|---|---|---|---|---|
| Composition of raw materials (g) | 4,4'-Diallyloxydiphenyl sulfone | | 250 | 90 | 250 | 250 |
| | Triphenylphosphine | | — | — | — | — |
| | Tri-n-octylphosphine | | — | — | — | — |
| | N,N-dimethylaniline | | 0.25 | 0.087 | — | — |
| | Trilauryl phosphite | | — | — | — | 0.25 |
| | Hydroquinone monomethyl ether | | 0.25 | 0.087 | 0.25 | — |
| | 3,5-Di-t-butyl-4-hydroxytoluene | | — | — | — | — |
| | 85% Phosphoric acid | | 0.07 | 0.026 | — | — |
| | Isoparaffinic hydrocarbon solvent | | — | 60 | — | — |
| | Paraffinic hydrocarbon solvent | | — | 60 | — | — |
| Reaction product | 3,3'-Diallyl-4,4'-dihydroxydiphenyl sulfone | Yield (%) | 92.2 | 82.8 | 6.2 | 3.9 |
| | | Coloration | D | C | C | D | sition presented in Table 1 were charged, and the reaction product was analyzed by HPLC. As a result, the yield of 3,3'-diallyl-4,4'-dihydroxydiphenyl sulfone of the target product was 92.2%. The color of the reaction product in a molten state was black.

Comparative Example 3

The reaction was conducted under the same conditions as in Example 1 except that raw materials having the composition presented in Table 1 were charged, and the reaction product was analyzed by HPLC. As a result, the yield of 3,3'-diallyl-4,4'-dihydroxydiphenyl sulfone of the target product was 82.8%. The color of the reaction product in a molten state was brown.

Comparative Example 4

The reaction was conducted under the same conditions as in Example 1 except that raw materials having the composition presented in Table 1 were charged, and the reaction product was analyzed by HPLC. As a result, the yield of 3,3'-diallyl-4,4'-dihydroxydiphenyl sulfone of the target product was 6.2%. The color of the reaction product in a molten state was brown.

Comparative Example 5

The reaction was conducted under the same conditions as in Example 1 except that raw materials having the composition presented in Table 1 were charged, and the reaction product was analyzed by HPLC. As a result, the yield of 3,3'-diallyl-4,4'-dihydroxydiphenyl sulfone of the target product was 3.9%. The color of the reaction product in a molten state was black.

From the results in Table 1, it is apparent that, according to the production process of the present invention, it is possible to suppress coloration and by-production of impurities at the time of the thermal rearrangement reaction of a diallyl etherified bisphenol compound and thus to obtain a high-quality allyl-substituted bisphenol compound at a high yield.

INDUSTRIAL APPLICABILITY

The allyl-substituted bisphenol compound obtained at a high yield by the production process of the present invention is less colored, and it is thus possible to decrease the amount of adsorbent to be used in the subsequent decoloration step or to omit the decoloration step itself. In addition, the allyl-substituted bisphenol compound according to the present invention contains impurities in a small amount, and it is thus possible to conveniently perform the purification step of the reaction product and to decrease the production loss of the target product and the production time. In other words, it is possible to more conveniently and easily produce an allyl-substituted bisphenol compound as compared to the conventional process.

The invention claimed is:
1. A process for producing an allyl-substituted bisphenol compound comprising:
a step of subjecting a diallyl etherified bisphenol compound represented by the following general formula (I) to a thermal rearrangement reaction in the presence of a phosphine compound represented by the following general formula (II):

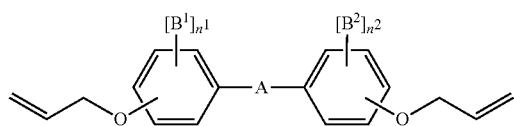
(I)

[in the formula, A represents a single bond, —SO$_2$—, —S—, —O—, a divalent group represented by the following formula (i-1), or a divalent group represented by —CY$^1$Y$^2$— (Y$^1$ and Y$^2$ each independently represent hydrogen, a linear, branched, or cyclic alkyl group having 6 or less carbon atoms, a phenyl group, or an aralkyl group having 7 or 8 carbon atoms), B$^1$ and B$^2$ each independently represent a linear, branched, or cyclic alkyl group having 6 or less carbon atoms, an allyl group, a phenyl group, or an aralkyl group having 7 or 8 carbon atoms, and n$^1$ and n$^2$ each independently represent an integer from 0 to 2,

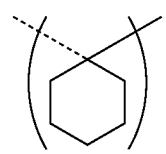
(i-1)]

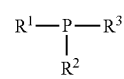
(II)

[in the formula, R$^1$, R$^2$, and R$^3$ each independently represent a linear, branched, or cyclic alkyl group having from 6 to 10 carbon atoms, an aryl group having from 6 to 14 carbon atoms, or an aralkyl group having 7 or 8 carbon atoms].

2. The production process according to claim 1, wherein an antioxidant is further present in the step.

\* \* \* \* \*